US010864297B2

(12) United States Patent
Procter et al.

(10) Patent No.: US 10,864,297 B2
(45) Date of Patent: Dec. 15, 2020

(54) METHOD OF MANUFACTURING AN IMPLANT FOR USE IN A SURGICAL PROCEDURE

(71) Applicant: Stryker European Holdings I, LLC, Kalamazoo, MI (US)

(72) Inventors: Philip Procter, Divonne les Bains (FR); Jan Henrik Sörensen, Kiel (DE); Hartwig Steckel, Hamburg (DE); Torben Christian Sörensen, Mönkeberg (DE); Ken Welch, Sigtuna (SE)

( * ) Notice: Subject to any disclaimer, the term of this patent is extended or adjusted under 35 U.S.C. 154(b) by 0 days.

(21) Appl. No.: 14/916,090

(22) PCT Filed: Sep. 2, 2013

(86) PCT No.: PCT/EP2013/068082
§ 371 (c)(1),
(2) Date: Mar. 2, 2016

(87) PCT Pub. No.: WO2015/028100
PCT Pub. Date: Mar. 5, 2015

(65) Prior Publication Data
US 2016/0220730 A1 Aug. 4, 2016

(51) Int. Cl.
| | | |
|---|---|---|
| *A61L 27/32* | (2006.01) | |
| *A61L 27/06* | (2006.01) | |
| *C25D 11/26* | (2006.01) | |
| *A61L 27/58* | (2006.01) | |
| *A61L 27/54* | (2006.01) | |
| *B05D 1/18* | (2006.01) | |
| *C23C 26/00* | (2006.01) | |
| *C23C 28/04* | (2006.01) | |

(52) U.S. Cl.
CPC .............. *A61L 27/32* (2013.01); *A61L 27/06* (2013.01); *A61L 27/54* (2013.01); *A61L 27/58* (2013.01); *B05D 1/18* (2013.01); *C23C 26/00* (2013.01); *C23C 28/042* (2013.01); *C25D 11/26* (2013.01); *A61L 2300/406* (2013.01); *A61L 2300/606* (2013.01); *A61L 2420/02* (2013.01)

(58) Field of Classification Search
CPC ...................................................... A61L 27/32
See application file for complete search history.

(56) References Cited

U.S. PATENT DOCUMENTS

| | | |
|---|---|---|
| 5,047,034 A | 9/1991 | Sohngen |
| 5,053,212 A | 10/1991 | Constantz et al. |
| 5,164,187 A | 11/1992 | Constantz et al. |
| 5,188,670 A | 2/1993 | Constantz |
| 5,279,831 A | 1/1994 | Constantz et al. |
| 5,964,932 A | 10/1999 | Ison et al. |
| 5,968,253 A | 10/1999 | Poser et al. |
| 6,053,970 A | 4/2000 | Ison et al. |
| 6,558,709 B2 | 5/2003 | Higham |
| 6,596,338 B2 | 7/2003 | Scott et al. |
| 6,821,528 B2 | 11/2004 | Scott et al. |
| 7,507,483 B2 | 3/2009 | Schwartz et al. |
| 2003/0049324 A1 | 3/2003 | Vogt et al. |
| 2003/0077381 A1 | 4/2003 | Scott et al. |
| 2006/0134160 A1 | 6/2006 | Troczynski et al. |
| 2007/0213832 A1 | 9/2007 | Wen |
| 2007/0259101 A1 | 11/2007 | Kleiner et al. |
| 2008/0306579 A1 | 12/2008 | Dolan et al. |
| 2009/0269480 A1 | 10/2009 | Berglund |
| 2010/0098632 A1* | 4/2010 | Russell .............. A61K 51/0489 424/1.77 |
| 2014/0308334 A1* | 10/2014 | Bhaduri .................. A61L 27/32 424/423 |

FOREIGN PATENT DOCUMENTS

| | | |
|---|---|---|
| CN | 101537208 A | 9/2009 |
| EP | 0806212 A1 | 11/1997 |
| WO | 2009100792 A2 | 8/2009 |
| WO | 2010126436 A1 | 11/2010 |
| WO | 2013013218 A2 | 1/2013 |
| WO | 2013067049 A1 | 5/2013 |
| WO | 2013072576 A1 | 5/2013 |

OTHER PUBLICATIONS

Szesz (Thin Solid Films 528 (2013) 163-166).*
Habibovic (J. Am. Ceram. Soc., 85 [3] 517-22 (2002)).*
Danco (http://www.danco.net/PDF-DOWNLOADS/TITANIUM%20II.pdf; 2003, downloaded Oct. 30, 2017).*
Ishizawa (Journal of Biomedical Materials Research, vol. 29, 1071-1079 (1995)).*
Lakstein (Acta Biomaterialia 5 (2009) 2258-2269).*
Stigter (Journal of Controlled Release 99 (2004) 127-137).*
"Non-Toxic and Bio-Compatible Type 2 Titanium Anodizing", 2003, XP055117504, Retrieved from the Internet: <URL: http://www.danco.net/PDF-DOWNLOADS/TITANIUM II. pdf>, [retrieved on May 12, 2014].

(Continued)

*Primary Examiner* — Devang K Thakor
(74) *Attorney, Agent, or Firm* — Lerner, David, Littenberg, Krumholz & Mentlik, LLP

(57) ABSTRACT

A method of manufacturing an implant for use in a surgical procedure, a corresponding implant and the use thereof during the incorporation of a substance is presented. Specifically anodized and blasted titanium implant substrates are provided with a hydroxyapatite (HA) coating for incorporating for example a therapeutic agent. In particular, an anodizing procedure by an electrolytic process in an alkaline liquid is carried out. Moreover, blasting of the anodized titanium implant substrate is carried out by the presented method. The HA coating can be in the range of 1 to 5 μm, particularly in the range of 1 to 3 μm. A local delivery of the active pharmaceutical ingredient is achieved by the implant of the present invention. Moreover, the implant allows for the removal of the implant without damaging surrounding tissue or a bone. Moreover, the HA coating is provided to the substrate such that enhanced fixation as measured by pull-out force is achieved whilst having a relatively low removal torque. The HA coating and drug incorporation may be carried out sequentially but also co-precipitation approach can be used.

19 Claims, 6 Drawing Sheets

(56) References Cited

OTHER PUBLICATIONS

Aberg et al, Bisphosphonate incorporation in surgical implant coatings by fast loading and co-precipitation at low drug concentrations, J Mater Sci: Mater Med (2009) 20:2053-2061.
Abtahl et al, A bisphosphonate-coating improves the fixation of metal implants in human bone, A randomized trial of dental implants, Bone 50 (2012) 1148-1151.
Brohede et al, Multifunctional implant coatings providing possibilities for fast antibiotics loading with subsequent slow release, J Mater Sci: Mater Med (2009) 20:1859-1867.
Brunski et al, Biomaterials and Biomechanics of Oral and Maxillofacial Implants: Current Status and Future Developments, The Inrternational Journal of Oral & Maxillofacial Implants, 2000. 15-46.
F. Chai et al, Antibacterial activation of hydroxyapatite (HA) with controlled porosity by different antibiotics, Biomolecular Engineering 24 (2007) 510-514.
Forsgren et al, Co-loading of bisphosphonates and antibiotics to a biomimetic hydroxyapatite coating, Biotechnol Lett (2011) 33 :1265-1268.
Hetrick et al, Reducing implant-related infections: active release strategies, I Chem. Soc. Rev., 2006, 35, 780-789.
Hutson et al, Infections in Periarticular Fractures of the Lower Extremity Treated with Tensioned Wire Hybrid Fixators, Journal of Orthopaedic Trauma vol. 12, No. 3, 1998, pp. 214-218.
International Search Report for Application No. PCT/EP2013/068082 dated May 26, 2014.
International Search Report for Application No. PCT/IB2014/060905 dated Jun. 26, 2014.
International Search Report for Application No. PCT/IB2014/062454 dated Sep. 29, 2014.
James M Anderson, Biological Responses to Materials, Annu. Rev. Mater. Res. 2001. 31:81-110.
Johan Forsgren et al, Formation and adhesion of biomimetic hydroxyapatite deposited on titanium substrates, Acta Biomaterialia 3 (2007) 980–984.
K.C. Baker et al, Growth, characterization and biocompatibility of bone-like calcium phosphate layers biomimetically deposited on metallic substrata, Materials Science and Engineering C 26 (2006) 1351-1360.
Lilja et al, Photocatalytic and antimicrobial properties of surgical implant coatings of titanium dioxide deposited though cathodic arc evaporation, Biotechnol Lett (2012) 34:2299-2305.
Liu et al, Water-based sol-gel synthesis of hydroxyapatite: process development, Biomaterials 22 (2001) 1721-1730.
M.P. Ginebra et al, Calcium phosphate cements as bone drug delivery systems: A review, Journal of Controlled Release 113 (2006) 102-110.
Ma et al, Electrophoretic deposition of porous hydroxyapatite scaffold, Biomaterials 24 (2003) 3505-3510.
Mahan et al, Factors in Pin Tract Infections, Department of Orthopedic Surgery, University of Louisville, Louisville, Ky., Mar. 1991 vol. 14 No. 3 V , pp. 305-308.
Masse et al, Prevention of Pin Track Infection in External Fixation with Silver Coated Pins: Clinical and Microbiological Results, J Biomed Mater Res (Appl Biomater) 53: 600-604, 2000.
Poelstra et al, Prophylactic treatment of gram-positive and gram-negative abdominal implant infections using locally delivered polyclonal antibodies, pp. 206-215.
Sergio Allegrini Jr., et al, Hydroxyapatite grafting promotes new bone formation and osseointegration of smooth titanium implants, Ann Anat 188 (2006) 143-151.
Stigter M et al: "Incorporation of different antibiotics into carbonated hydroxyapatite coatings on titanium implants. release and antibiotic efficacy", Journal of Controlled Release, Elsevier, Amsterdam, NL, vol. 99, No. 1, Sep. 14, 2004 (Sep. 14, 2004). pp. 127-137, XP004549075.
Stigter M et al: "Incorporation of tobramycin into biomimetic hydroxyapatite coating on titanium", Biomaterials. Elsevier Science Publishers BV, Barking, GB, vol. 23, No. 20, Oct. 1, 2002 (Oct. 1, 2002), pp. 4143-4153. XP004370405.
Tengvalla et al, Surface immobilized bisphosphonate improves stainless-steel screw fixation in rats, biomaterials 25 (2004) 2133-2138.
Ulrika Brohede et al: "Multifunctional implant coatings providing possibilities for fast antibiotics loading with subsequent slow release", Journal of Materials Science: Materials in Medicine, Kluwer Academic Publishers, BO, vol. 20, No. 9, 28 Apr. 1 2009 (Apr. 28, 2009) pp. 1859-1867, XP019730963.
Zilberman et al, Antibiotic-eluting medical devices for various applications, journal of Controlled Release 130 (2008) 202-215.
Sörensen et al., "Biomechanical and antibacterial properties of Tobramycin loaded hydroxyapatite coated fixation pins", Journal of Biomedical Materials Research B: Applied Biomaterials, 2014, vol. 00B, Issue 00, 12 pages.
Sörensen et al., "Biomimetic Hydroxyapatite Coated Titanium Screws Demonstrate Rapid Implant Stabilization and Safe Removal In-Vivo", Journal of Biomaterials and Nanobiotechnology, 2015, 6, 20-35.

* cited by examiner 10 minutes 40 minutes

METHOD OF MANUFACTURING AN IMPLANT FOR USE IN A SURGICAL PROCEDURE

CROSS-REFERENCE TO RELATED APPLICATIONS

The present application is a national phase entry under 35 U.S.C. § 371 of International Application No. PCT/EP2013/068082 filed Sep. 2, 2013, published as WO 2015/028100 A1, which is hereby incorporated herein by reference.

FIELD OF THE INVENTION

The present invention relates to implants. In particular, the present invention relates to a method of manufacturing an implant for use in a surgical procedure, an implant for use in a surgical procedure and the use of an implant.

BACKGROUND OF THE INVENTION

In orthopedics and traumatology, reconstruction and preservation of the injured musculosceletal system and associated organs are in the focus of interest. Implant loosening, migration, cut-out as well as infection control play a major role in complications that may occur post-surgery. Bacterial infections after introduction of an implant to the body are usually caused by adherence of bacteria on the implant surface and subsequent bio film formation. On approximately 90% of all implants gram-positive microorganisms *Staphylococcus aureus* and *Staphylococcus epidermidis* can be found. Fracture fixation devices have a risk to get infected. The consequences of infected pin sites are pin loosening, fracture destabilization, and osteomyelitis, which in addition to human pain and suffering are costly and difficult to treat. To minimize implant related infections, systematic antibiotics are administered 2 to 14 days post-surgery with additional oral prophylaxis. However, systemic therapies have the possible disadvantage of not being sufficiently effective due to impaired blood circulation and the need for a high concentration of antibiotics.

Thus, new implant materials combining excellent mechanical properties, biodegradability and improved biocompatibility are desired in orthopaedic and trauma surgery. Over the last few years, new strategies have been proposed to control and prevent microbial contamination of implants. One of the promising approaches is the local treatment of implant-associated infections by using hydroxyapatite (HA) coatings for antibiotics delivery, exploiting the osteoconductive properties of this material.

The most common and widely reported method of HA coating deposition method is the plasma spraying technique. Due to the high temperatures used during spraying, HA coatings produced by this method have considerable disadvantages such as great coating thicknesses of 50 µm to 200 µm, alterations in the HA structure and poor adhesion between the coatings and metallic substrates, which influence the long-term clinical application of plasma-sprayed HA coatings. The rather dense structure of these HA coatings has shown limiting ability in terms of antibiotic incorporation using an adsorptive loading method.

SUMMARY OF THE INVENTION

The object of the present invention may be seen in providing an improved implant.

The object of the present invention is solved by the subject-matter of the independent claims. Further embodiments and advantages of the invention are incorporated in the dependent claims.

The described embodiments similarly pertain to method of manufacturing an implant for use in a surgical procedure, the implant and the use of an implant. Synergetic effects may arise from different combinations of the embodiments although they might not be described in detail.

Further on, it shall be noted that all embodiments of the present invention concerning a method, might be carried out with the order of the steps as described, nevertheless this has not to be the only and essential order of the steps of the method. The skilled person gathers all kinds of different orders and combinations of the method steps described herein, unless explicitly mentioned to the contrary hereinafter.

According to an exemplary embodiment of the invention, a method of manufacturing an implant for use in a surgical procedure is presented. The method comprises the steps of providing a titanium implant substrate and anodizing the titanium implant substrate by an electrolytic process in an alkaline liquid. Moreover, the step of blasting the anodized titanium implant substrate and the step of coating the blasted and anodized substrate with hydroxyapatite (HA) leading to a hydroxyapatite coating are comprised by the method.

In other words, if the above-defined method is carried out by the skilled person, an implant for use in a surgical procedure is manufactured wherein the implant comprises a titanium substrate with an anodized titanium surface. The anodized titanium surface can be anodized and blasted by a titanium type II anodizing process. Thus, $TiO_2$ coated implants are used in the present invention. The presented method allows for a manufacturing of implants with a thin or even ultra-thin HA coating, for example in the range of 0.5 µm to 5 µm, which coating allows for local delivery of active pharmaceutical ingredients like for example antibiotics or bisphosphonates. Other examples of therapeutic agents will be given in the following. The presented method allows the provision of HA coatings that demonstrate faster early stabilization and therefore, enhanced fixation as measured by pull-out force and removal torque measurements in-vivo, whilst having a relatively low removal torque and being able to safely remove the implant without extensive damage of the bone, the implant, the surgical equipment or the surrounding tissue.

In general, the HA coating of the present invention provides a fast stabilization but is still safely removable after full osseointegration, which is a unique characteristic. Further details and explanations about the various advantages of the present invention will be provided hereinafter.

The presented method may also be seen as a method for providing an implant interface, or providing an implant with a HA coating. The coating may be carried out such that a porous HA coating is provided on the surface of the implant. Moreover, the coating can be carried out by using a chemical biomimetic method. Different parameters for the step of anodizing and blasting can be used. However, preferable may be the standard set out in AMS 2488-D which leads to the known type II anodized titanium implant substrate. Thus, the presented method allows particularly for the provision for an ultra-thin biomimetic hydroxyapatite coating on anodized type II titanium implants which have an TiO2 coating.

It should be noted that in the context of the present invention the term "blasting" shall be understood as directing particles towards the surface of the implant to treat the surface accordingly. If desired, abrasive blasting can be used which abrasive material is forceably propelled against the surface under a pressure to smooth a rough surface, roughen a smooth surface, shape the surface, or remove surface contaminants. There are variants of the process, such as bead blasting, sandblasting, soda blasting and chop blasting. In particular, blasting according to the standard AMS 2488-D which leads to titanium anodized surfaces of type II can be used according to the present invention.

If desired, a cleaning process may be part of the method such that the anodized and blasted substrate is cleaned. The cleaning process may comprise soaking the implant in, for example, acetone, ethanol, and/or deionized water. Moreover, generating the HA coating on the titanium implant substrate can be carried out directly after blasting and/or directly after the cleaning process. In this case this case the implant substrate will be described in the following as "untreated" substrate or implant, as no NaOH pre-treatment, i.e. before the deposition of the HA coating, is carried out. However, in further particular embodiments, also a NaOH pre-treatment may be carried out, for example, after the cleaning process. In particular, such a NaOH pre-treatment may be carried out such that no significant change in morphology and/or roughness is caused on the titanium implant substrate. Details and explanations about such a NaOH pre-treatment will be provided hereinafter. However, it should be noted that the method of the present invention does not necessarily need such a NaOH pre-treatment. The inventors of the present invention were the first to deposit HA coatings on untreated type II oxidized titanium implants. It has been found by the present inventors that untreated type II implant surfaces can be used for depositing of HA coatings. In an exemplary embodiment, temperatures above 37° are used to obtain said HA coating on the $TiO_2$ coated implants.

The following different advantages and technical effects can be achieved with the present invention. No NaOH pre-treatment is necessary for the HA coating deposition and process temperatures above 37° C. can be used. If desired, the user may apply a NaOH pre-treatment of the substrate which can be very short and which does not alter the surface microstructure of the substrate. This is an important benefit compared to the prior art methods. In optimized NaOH pre-treatments a process time of only 5 to 10 minutes, or even less, can be achieved, which results in a large time saving compared to known methods. Furthermore, optimal thicknesses of 1 µm to 5 µm, or 1 µm to 3 µm of the HA coating can be achieved without self cracking. An unexpected feature is also that the growth of the coatings tends to even out the underlying roughness, which leads to a smoothening effect. Moreover, a special drug loading with pressure under evaluated temperature is presented. For example, 6 bar pressure and 90° C. may be used during the incorporation of the drug. Due to this specific drug loading, the release time of the drug in the body of the patient is increased as deeper pores are reached during the loading.

Further, a co-precipitation approach can be used. This approach combines the biomimetic growth of HA with incorporation of an active pharmaceutical ingredient or ions at the time of nucleation. In summary, the ingredients or ions to be incorporated are present during the biomimetic coating process. As an outcome of the process, the implant is coated with HA which simultaneously incorporates the therapeutic ingredient or ion by co-precipitation during manufacturing. Therefore, no additional drug or ion loading of the HA coating is necessary.

Furthermore, when applying stirring during the deposition of the HA coating, an increase of homogeneity in the HA coating is achieved and less agglomerates are built. An exemplary embodiment uses a stirring frequency of 325 rpm. In general, the HA coating of the present invention provides a fast stabilization but is still safely removable after full osseointegration, which is a unique characteristic.

The method may be seen as a biomimetic deposition that allows producing thinner, resorbable, nanoporous HA coatings at low temperatures, which allow creating an excellent drug delivery vehicle for antibiotics, growth factors and other ingredients. Functionalizing implant surfaces with HA coatings offering an on-demand, controlled drug release presents an interesting and powerful therapeutic tool to effectively reduce bacterial contamination.

According to another exemplary embodiment of the invention, the titanium implant substrate is formed of titanium alloy Ti6A1-4V.

Ti6A1-4V, Ti6A1-4V, Ti-6A1-4V or Ti 6-4 is a Ti alloy. It has a chemical composition of 6% aluminum, 4% vanadium, 0.25% (maximum) iron, 0.2% (maximum) oxygen, and the remainder titanium. It is significantly stronger than commercially pure titanium while having the same stiffness and thermal properties. Among its many advantages, it is heat treatable. This grade is an excellent combination of strength, corrosion resistance, weld and fabricability. Generally, Ti-6A1-4V can be used in applications up to 400 degrees Celsius. It has a density of about 4420 $kg/m^3$, Young's modulus of 110 GPa, and tensile strength of 1000 MPa. By comparison, annealed type 316 stainless steel has a density of 8000 $kg/m^3$, modulus of 193 GPa, and tensile strength of only 570 MPa. And tempered 6061 aluminum alloy has 2700 $kg/m^3$, 69 GPa, and 310 MPa, respectively. Moreover, in case the anodizing the blasting steps are carried out according to AMS 2488-D, this titanium alloy is preferred. As will become apparent from and elucidated with further explanations, this Ti alloy in combination with the type II anodization leads to specific advantages of the HA coated implant.

According to another exemplary embodiment of the invention, the steps anodizing and blasting are carried out according to AMS 2488-D resulting in a type II anodized titanium implant substrate.

In other words, the previously defined steps of "providing a titanium implant substrate, anodizing the titanium implant substrate by an electrolytic process in an alkaline liquid, and blasting the anodized titanium implant substrate" can be seen in this embodiment as the step of "providing for a type II anodized titanium implant substrate". This substrate can subsequently be used for carrying out the defined step of coating the substrate with hydroxyapatite (HA) leading to the HA coating.

Moreover, Ti6A14V implants with type-II-anodization treatment are showing a superior corrosion resistance which can be equated with excellent biocompatibility properties. In addition to positively influenced bony ingrowth behaviour, an increased anti-infection efficacy is shown. Similar benefits for the type-II-anodization treatment are also demonstrated by enhanced biomechanical properties. Compared to untreated implants, the fatigue strength is increased by 15% and the wear and friction characteristics are significantly improved. The titanium alloy Ti6A14V with type-II-anodization treatment provides an excellent suitability for implants used in traumatological application.

Regarding the term type-II-anodization treatment and type II anodized titanium implant substrate; the skilled person is familiar of the anodization and the blasting of this procedure. Nevertheless, in the following some more detailed explanations in this respect are provided. Anodic treatment of titanium and titanium alloys for implant products known as "Type 2" anodization is typically performed according to AMS 2488-D. The anodization process accelerates the formation of an oxide coating under controlled conditions to provide the desired result. The coating may be created using various electrolytes where the parts are made positive (anodic) with a corresponding negative (cathodic) terminal attached to a D.C. power supply. Electrolytic solutions may vary from one processor to another but must be of pH 13 or higher to conform to specification requirements. The implant may be racked appropriately on, e.g., titanium racks, to create electrical contact. The implant may be alkaline cleaned to remove any machine oils. The implant is immersed in the electrolyte; current is applied with the voltage being raised to maintain the required current density during processing. This voltage varies for different alloys and with the capacity and design parameters of the installed equipment. The implant may be rinsed, dried and the excess slough can be removed. As the process creates a penetrating coating, there is no measurable dimensional change when measured with a micrometer accurate to 0.0001 inch (2.5 µm). Quality inspection can be performed on the completed implant. Per AMS 2488-D, anodic coating, as received by purchaser, shall be continuous, smooth, adherent to basis metal, uniform in texture and appearance, and free from burned or powdery areas, loose films, discontinuities, such as breaks or scratches, except at contact points or other damage or imperfections detrimental to usage of the coating.

According to another exemplary embodiment of the invention, the step of coating the substrate with HA is based on crystal growth of HA on a surface of the implant.

An unexpected feature of the growth of the coatings in crystal form is that it tends to even out the underlying roughness. The prior art completely neglects the roughness of titanium implants and testing has been done on polished or machined surfaces.

Here, the type II surfaces are rough due to the anodization procedure and the coating process strives to even out the roughness, thus valleys in the surface is filled first with the biomimetic coating and hills have a thinner HA layer initially.

According to another exemplary embodiment of the invention, the HA coating is deposited from a solution or from an aqueous solution containing ions.

In a specific exemplary embodiment, the HA deposition may use a 72 h storage in the solution, e.g. in Dulbecco's PBS buffer solution D 8662 at 70° C. This buffer is a phosphate buffered saline supplied by Sigma, Steinheim, Germany. The PBS contained $CaCl_2$ and $MgCl_2$ as ion source. For example, a holder may be used which prevents coating of particular parts of the implant. For example, in case of screws or pins as implants, the holder may prevent coating the screw heads. However, also other implant embodiments besides screws are part of the present invention. If desired, stirring of the PBS with, for example, a magnetic steer bar can be adjusted to minimize the formation of HA aggregates on the HA coating. Furthermore, when applying stirring during the deposition of the HA coating, an increase of homogeneity in the HA coating is achieved and less agglomerates are built. An exemplary embodiment uses a stirring frequency of 325 rpm. After removal from the solution, the implant can be removed from the holder, rinsed in deionized water and dried with a flow of nitrogen. More details about and aspects of this HA deposition will be given herein, in particular in the context of the described example.

According to another exemplary embodiment of the invention, the titanium implant substrate is inserted into the solution for a time period t. Furthermore, the time period t is selected from the group comprising between 20 h and 80 h, between 40 h and 80 h, between 60 h and 80 h, between 65 h and 75 h, between 70 h and 75 h, and 72 h.

Optimal soaking times have been found, i.e. the time period needed for a thick enough coating but not with a thickness that give self cracking.

According to another exemplary embodiment of the invention, the solution has a temperature above 37° C., between 40° C. and 85° C., between 50° C. and 80° C., between 65° C. and 75° C., or 70° C.

In particular, for untreated type II anodized titanium implant substrate surfaces it is not obvious that solution temperatures above 37° lead to positive deposition results. The combination of untreated type II oxidized titanium implant and a hydroxyapatite solution having a temperature above 37° facilitates ultrathin HA coatings in the range of 0.5 to 5 µm thicknesses in crystalline form. Such an implant allows for an effective incorporation of substances like therapeutic agents, pharmaceutical agents or the like as will be defined in more detail hereinafter. Moreover, such a coating evens out the underlying roughness of the substrate. The coatings achieved with this embodiment of the present invention allow removing the implant from the body of the patient without damaging surrounding bone and without damaging the implant itself as has been described before.

According to another exemplary embodiment of the invention, the HA coating has a crystalline structure and the coating has a thickness which is between 0.5 µm and 5 µm or between 1 µm and 3 µm.

According to another exemplary embodiment of the invention, the method comprises the step of inserting the titanium implant substrate into a NaOH solution before the step of coating the substrate with a HA coating. Furthermore, the titanium implant substrate is kept in the NaOH solution for a time period t, wherein the time period t is selected from the group comprising between 1 and 20 minutes, between 5 and 15 minutes, between 8 and 12 minutes, between 9 and 11 minutes, and 10 minutes.

In particular, the NaOH pre-treatment can be adjusted by the user according to the present invention such that no significant change in morphology or roughness of the implant is caused. Compared to the prior art pre-treatments, the present invention allows for a significant reduction of the time needed for the NaOH pre-treatment. This allows the manufacturer to reduce the production costs per implant.

The inventors have been able to demonstrate that the pre-treatment described in here does not alter the surface microstructure to a large degree. Via optimized pre-treatment parameters as given herein a substantially unaffected type II surface of the implant is achieved but with a higher nucleation and growth rate of the coating than for the untreated surface.

According to another exemplary embodiment of the invention, a surface of the blasted substrate is not treated, particularly not with a NaOH solution, before the step of coating the substrate with a HA coating. As has been described before and will be described hereinafter, the present invention also allows for avoidance of a NaOH pre-treatment in accordance with specific embodiments of the present invention. Advantageously, also time and costs for the manufacturer are saved by these exemplary embodiments of the invention.

According to another exemplary embodiment of the invention, the method further comprises the step of incorporating a substance into the HA coating. Moreover, the substance is selected from the group comprising a therapeutic agent, an osteoporotic drugs, bisphosphonates, strontium, PTH, antibiotics, gentamycin, tobramycin, vancomycin, doxycycline, chemotherapy drugs, analgetics, antiphlogistics, metal ions, copper ions, silver ions, organic molecules, and any combination thereof.

Different pharmaceutical ingredients like for example antibiotics or bisphosphonates are part of the present invention. This allows an advantageous local delivery of these active pharmaceutical ingredients. Moreover, a special drug loading or incorporation with pressure and under evaluated temperature is presented. For example, 6 bar pressure and 90° C. may be used during the incorporation of the drug. Due to this specific drug loading, the release time of the drug in the body of the patient is increased as deeper pores in the coating are reached during the loading.

According to another exemplary embodiment of the invention the drug loading is carried out at a temperature which is between 50° C. and 100° C. and at a pressure which is between 3 and 20 bar.

According to another exemplary embodiment of the invention, an implant for use in a surgical procedure is presented. The implant comprises a titanium implant substrate, wherein the titanium implant substrate has an anodized and a blasted surface and a HA coating on said surface.

According to another exemplary embodiment of the invention, the titanium implant substrate is formed of the titanium alloy Ti6A1-4V.

According to another exemplary embodiment of the invention, the titanium implant substrate is anodized and blasted according to AMS 2488-D resulting in a type II anodized titanium implant substrate.

According to another exemplary embodiment the implant has surface roughness after the NaOH pre-treatment described by $R_z$ which is smaller than 4.

It should be noted that the Ra/Rz value after NaOH pretreatment may not change since these changes are small compared to the roughness of the e.g. type II surface According to another exemplary embodiment of the invention, the titanium implant substrate is a screw, plate, nail or any other type of surgical implant.

According to another exemplary embodiment of the invention, the use of a type II anodized titanium implant during the incorporation of a substance into the HA coating is presented, wherein the substance is selected from the group comprising a therapeutic agent, an osteoporotic drug, bisphosphonates, strontium, PTH, antibiotics, gentamycin, tobramycin, vancomycin, doxycycline, a chemotherapy drug, analgetics, antiphlogistics, metal ions, copper ions, silver ions, organic molecules, and any combination thereof.

According to another exemplary embodiment a computer program element is provided which can be used to cause the method of manufacturing to produce the desired implant. Such a computer program element may be stored on an apparatus which carries out the desired manufacturing method. Such a computer program element may also be stored on a computer-readable medium. The computer program element may be part of a computer program, but it can also be an entire program by itself. For example the computer program element may be used to update an already existing computer program to get to the present invention. A computer program may be stored/distributed on a suitable medium such as an optical storage medium or a solid-state medium supplied together with or as part of other hardware, but may also be distributed in other forms, such as via the Internet or other wired or wireless telecommunication systems. The computer readable medium may be seen as a storage medium, such as for example, a USB stick, a CD, a DVD, a data storage device, a hard disk, or any other medium on which a program element as described above can be stored.

It may be seen as a gist of the invention to provide for an ultra-thin, biomimetic hydroxyapatite coating on anodized type II titanium implant. These and other features of the invention will become apparent from and elucidated with reference to the embodiments described hereinafter. Further, the herein presented method may also be seen as a method for providing an implant interface, or providing an implant with a HA coating.

The figures are schematic and not on scale.

DETAILED DESCRIPTION OF EMBODIMENTS

Figure 1:
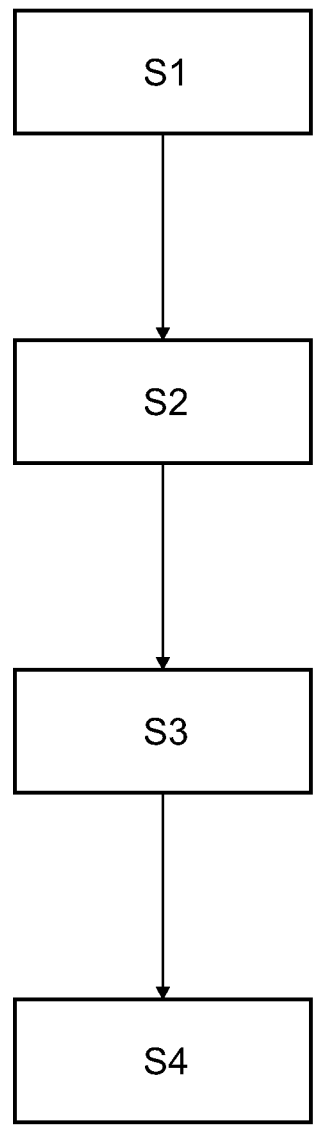
FIG. 1 schematically shows a flow diagram of a manufacturing method according to an exemplary embodiment of the present invention.

FIG. 1 schematically shows a method of manufacturing an implant for use in a surgical procedure according to an exemplary embodiment of the present invention. The titanium implant substrate, for example a Ti6A1-4V substrate, is provided. This provision of the substrate is shown with step S1 whereas step S2 depicts the anodization of this substrate by an electrolytic process in an alkaline liquid. Preferably, this anodization step may be carried out in accordance with the standard defined by AMS 2488-D. Moreover, the method of FIG. 1 comprises the blasting of the anodized titanium implant substrate in step S3. Also this step can preferably be embodied as the blasting step defined in AMS 2488-D. Moreover, the blasted and anodized substrate is subsequently coated with a hydroxyapatite (HA) layer/coating in step S4. The implant manufactured by the method of FIG. 1 provides the advantage that the coating remains within the body of the patient when the implant is removed from the body. In particular, either the coating has been dissolved within the body or the coating is separated from the titanium implant substrate during the removal of the implant. In particular, the HA coating of the implant of the present invention demonstrates enhanced fixation as measured by pull-out force whilst having a relatively low removal torque. The HA coating of the present invention can be embodied as very thin porous coating and can be deposited during the usage of a chemical biomimetic method. In different embodiments which can be derived from the embodiment of FIG. 1, a cleaning process may used in addition. Moreover, if desired, a NaOH pre-treatment, as has been described before, can be comprised, but is not mandatory. Furthermore, the use of a type II anodized titanium implant during the incorporation of a medical or pharmaceutical product into the HA coating of the implant can be combined with the method of FIG. 1. The method of FIG. 1 may also be seen as a method for providing an implant interface, or providing an implant with a HA coating.

Figure 2:
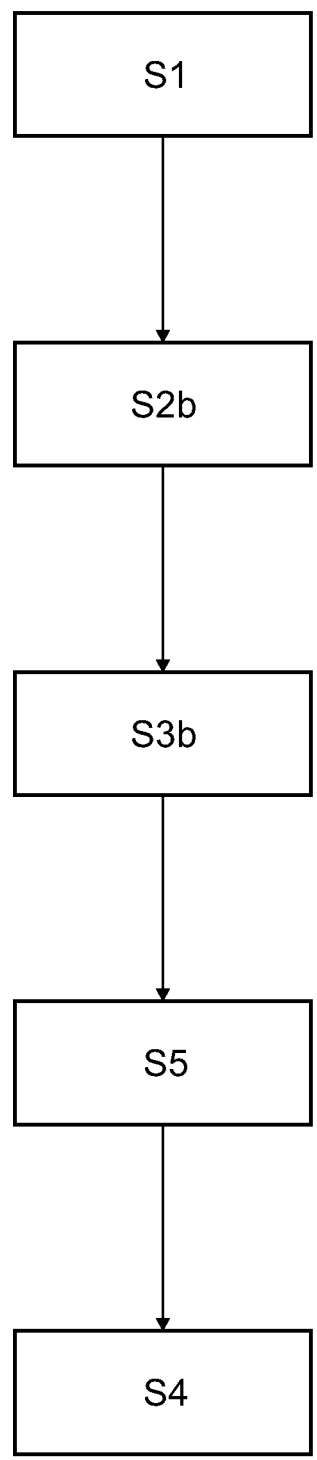
FIG. 2 schematically shows a flow diagram of a manufacturing method according to another exemplary embodiment of the present invention.

According to a further specified embodiment, FIG. 2 shows a flow diagram of a manufacturing method. In particular, for steps S1 and S4 it is referred to the descriptions of FIG. 1. After step S1, a specific anodization S2b of the titanium implant substrate by an electrolytic process in an alkaline liquid as defined by AMS 2488-D is carried out. Moreover, blasting step S3b is carried out according to AMS 2488-D standard. In the embodiment of FIG. 2 also a NaOH pre-treatment is carried out in step S5. The titanium implant substrate is inserted into a NaOH solution before the step of coating, which is carried out in step S4. Thereby, the titanium implant substrate is kept in the NaOH solution for 10 minutes. However, in other exemplary embodiments other time periods as described herein for the NaOH pre-treatment may be used by the skilled person.

Figure 3:
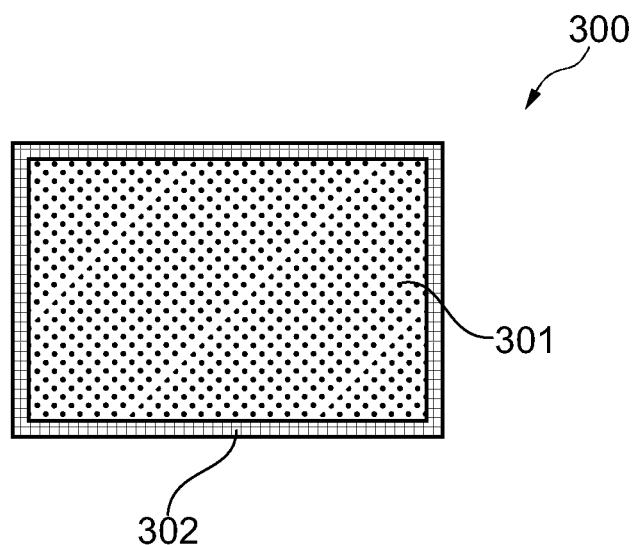
FIG. 3 shows a type II anodized titanium implant substrate with a bioactive surface according to an exemplary embodiment of the present invention.

FIG. 3 shows an implant 300 according to the present invention. The implant 300 is manufactured by the presented method and provides the advantage that the coating remains within the body of the patient when the implant is removed from the body. FIG. 3 shows a titanium implant substrate 301 which comprises a bioactive surface 302. The substrate 301 is a type II anodized substrate, as has been described before in detail. The bioactive surface 302 may be provided via a NaOH pre-treatment as has been described with different parameters before. For example, a 10 minutes soaking step in 5 M NaOH solution at 70° C. may be used. No significant change in the morphology or roughness of the substrate 301 is caused.

Figure 4:
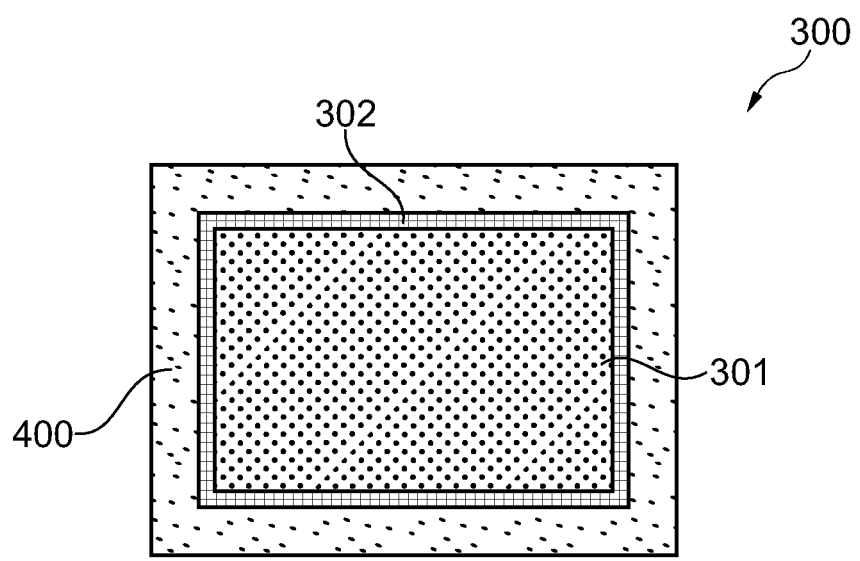
FIG. 4 shows the implant of FIG. 3 after depositing a crystalline, HA coating on the implant.

FIG. 4 schematically shows the implant 300 as described with respect to FIG. 3. In addition to the substrate 301 and the bioactive surface 302, a HA coating 400 is shown. This coating is ultrathin and in the range of 1 to 3 μm. Moreover, the HA coating is provided in a crystalline form. Such a thin and porous coating 400 allows for a local delivery of active pharmaceutical ingredients and allows removing subsequently the implant without damaging surrounding bone. The used NaOH pre-treatment of the substrate can be very short and does not alter the surface microstructure of the substrate. Furthermore, the ultrathin thicknesses can be achieved without self cracking. An unexpected feature is also that the growth of the coatings tends to even out the underlying roughness, which leads to a smoothening effect. Moreover, a special drug loading with pressure under evaluated temperature can be applied subsequently.

Figure 5:
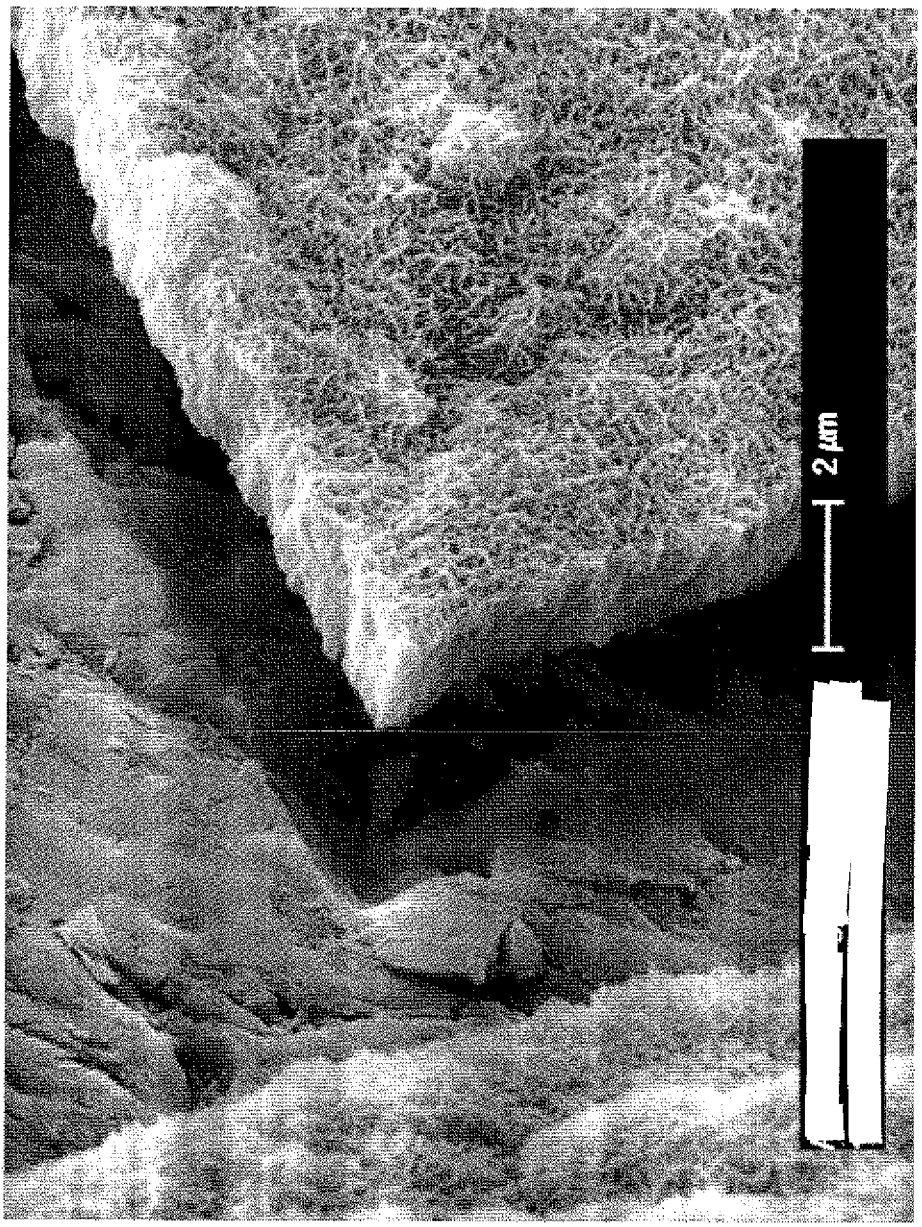
FIG. 5 schematically shows an SEM image of an HA coating according to exemplary embodiment of the present invention.

FIG. 5 shows a scanning electron microscope image (SEM) of an implant having an HA coating according to the present invention. FIG. 5 shows an untreated surface of the titanium implant substrate which can be observed in the underlying surface. In other words, in the example of FIG. 5, no NaOH pre-treatment was carried out.

Furthermore, the HA coating is depicted in FIG. 5 showing a coating thickness of approx 1.5 μm and a nanoporous microstructure.

Figure 6:
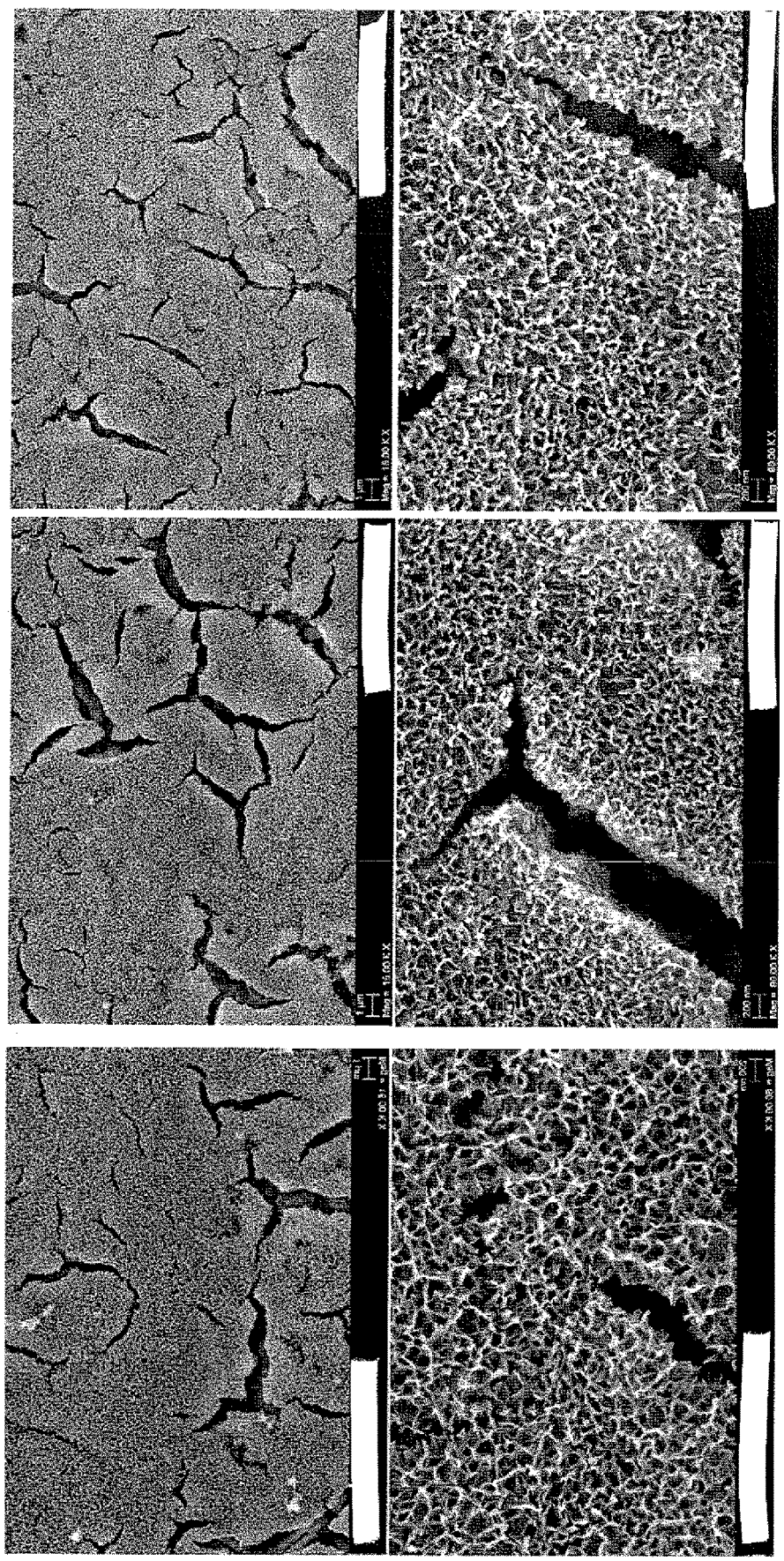
FIG. 6 schematically shows SEM images of implant surfaces resulting from different NaOH pre-treatments.

FIG. 6 shows the impact of NaOH treatment on an type II anodized titanium surface after storage in NaOH solution for different time points, namely 9 h, 3 h, and 1 h, by SEM imaging. For each time period two different magnifications are presented. NaOH pre-treatment for all durations resulted in changes of the surface structure. The longer the treatment duration the greater is the impact on the surface. Additionally several cracks can be observed for all time points tested.

Figure 7:
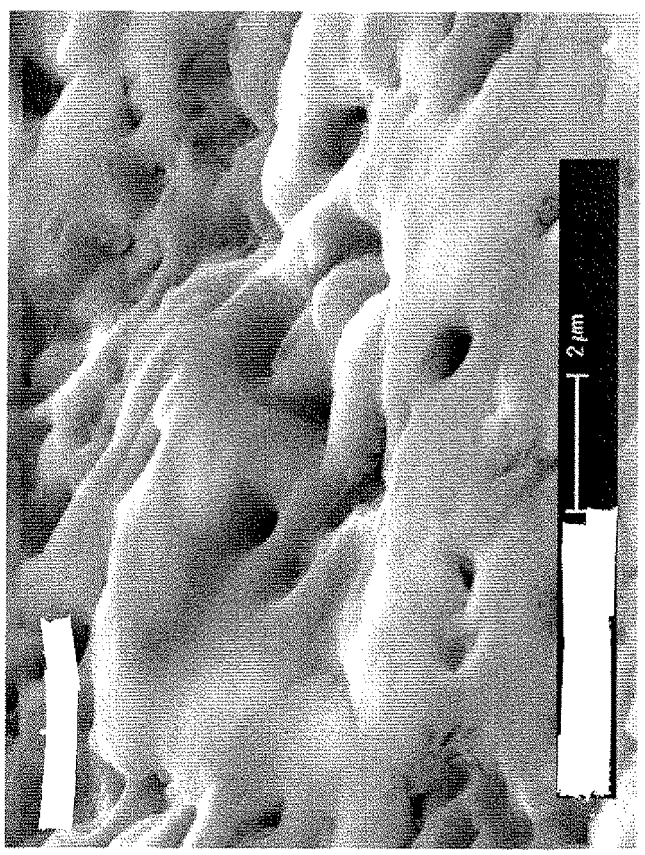
FIG. 7 schematically shows SEM images of implant surfaces resulting from different NaOH pre-treatments.
Figure 7:
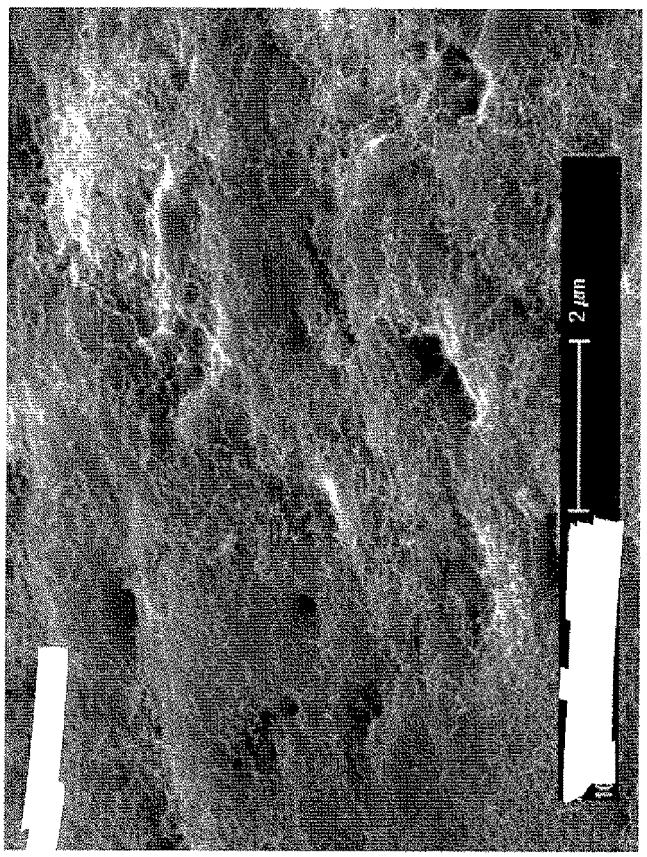

FIG. 7 schematically shows SEM images of implant surfaces resulting from different time durations of NaOH pre-treatments, namely 40 and 10 minutes. After 40 minutes minor changes in surfaces morphology and minor self-cracking can be observed. After 10 minutes of NaOH pre-treatment nearly no morphological change was demonstrated by SEM analyses.

EXAMPLE

In the following an exemplary process of depositing hydroxyapatite on an anodized type II titanium implant will be described, as well as an exemplary incorporation process for incorporating an antibiotic substance into such a HA coating.

A biomimetic hydroxyapatite coating is deposited on anodized type II titanium implants by a biomimetic method. The implant, both untreated and NaOH treated as described herein, were soaked in phosphate buffered saline (PBS) (Dulbecco's PBS, Sigma, Steinheim, Germany) for a defined time period at a defined temperature. In this Example, a 72 h storage in the solution at 70° C. was used. The HA coating was biomimetically precipitated on the $TiO_2$ coated pins using PBS containing $CaCl_2$ and $MgCl_2$ as ion source. Screws for example were often placed in a system with the tips hanging down. The beaker container for examples had a volume of 100 ml of PBS.

The PBS was constantly stirred during the deposition process with a magnetic stir bar to ensure a more even HA coating. After removal from the PBS solution, the implants were rinsed in deionized water and dried with a flow of $N_2$. In this example the PBS solution D 8662 as described below was used. Different other PBS solutions comprising $CaCl_2$ and $MgCl_2$ as summarized in the following can also be used. However, also other solutions may be used for the HA coating/deposition in accordance with the present invention:

| DULBECCO'S PHOSPHATE BUFFERED SALINE | | | | | |
|---|---|---|---|---|---|
| COMPONENT | D 8662<br>D 5780<br>[1X]<br>g/L | D 5773<br>g/L | D 5652<br>g/L | D 7030<br>g/L | D 5527<br>D 8537<br>[1X]<br>g/L |
| INORGANIC SALTS | | | | | |
| $CaCl_2 \cdot 2H_2O$ | 0.133 | — | — | — | — |
| $MgCl_2 \cdot 6H_2O$ | 0.1 | 0.1 | — | — | — |
| KCl | 0.2 | 0.2 | 0.2 | 0.2 | 0.2 |
| $KH_2PO_4$ (anhyd) | 0.2 | 0.2 | 0.2 | 0.2 | 0.2 |
| NaCl | 8.0 | 8.0 | 8.0 | 8.0 | 8.0 |
| $Na_2HPO_4$ (anhyd) | 1.15 | 1.15 | 1.15 | 1.15 | 1.15 |
| Grams of powder required to prepare 1 L | N/A | 9.7 | 9.6 | 9.6 | N/A |

| COMPONENT | D 6650<br>g/L | D 4031<br>[1X]<br>g/L | D 1283<br>[10X]<br>g/L | D 1408<br>[10X]<br>g/L |
|---|---|---|---|---|
| INORGANIC SALTS | | | | |
| $CaCl_2 \cdot 2H_2O$ | 0.133* | 0.133 | 1.33 | — |
| $MgCl_2 \cdot 6H_2O$ | 0.1 | 0.1 | 1.0 | — |
| KCl | 0.2 | 0.2 | 2.0 | 2.0 |
| $KH_2PO_4$ (anhydrous) | 0.2 | 0.2 | 2.0 | 2.0 |
| NaCl | 8.0 | 8.0 | 80.0 | 80.0 |
| $Na_2HPO_4$ (anhyd) | 1.15 | 1.15 | 11.5 | 11.5 |

-continued

| DULBECCO'S PHOSPHATE BUFFERED SALINE | | | | |
|---|---|---|---|---|
| OTHER | | | | |
| D-Glucose | 1.0 | 1.0 | — | — |
| Kanamycin Sulfate | — | 0.1 | — | — |
| Penicillin G (sulfate) | $10^6$ units* | — | — | — |
| Pyruvic Acid•Na | 0.036 | 0.036 | — | — |
| Streptomycin Sulfate | 0.05 | 0.05 | — | — |

*Supplied separately

Moreover, such HA coated implant can be loaded with e.g. Tobramycin by the following loading procedure. As an example, Ti bone screws were loaded by adsorption in Tobramycin containing water of double distilled quality at a concentration of e.g. 4 mg/ml, 20 mg/ml or 40 mg/ml. Loading at room temperature was performed by filling a test tube with 2 ml of Tobramycin stock solution, transferring the sample into the test tube for a loading time of 5 minutes. Afterwards the screw was removed by the help of an artery clamp and dried in an oven for 24 hours at 37° C. in a vertical position. The loading under temperature and pressure were prepared by placing the HA-coated implants in 30 ml of stock solution containing e.g. 4 mg/ml, 20 mg/ml or 40 mg/ml Tobramycin in a stainless steel tube under an applied pressure. The elevated temperature prevailing during loading was ensured by preheating the steel tube and the stock solution prior to the loading procedure. The loaded implants were placed in an oven for drying. Thus, in a first alternative, the loading is carried after depositing the HA coating and can be carried out by inserting the HA coated implant into the antibiotic solution. Further, as a second alternative, also an simultaneous incorporation and HA coating process can be used. This has been described before as a co-precipitation approach, which approach combines the biomimetic growth of HA with incorporation of an active pharmaceutical ingredient or ions at the time of nucleation. In summary, the ingredients or ions to be incorporated are present during the biomimetic coating process. As an outcome of the process, the implant is coated with HA which simultaneously incorporates the therapeutic ingredient or ion by co-precipitation during manufacturing. Therefore, no additional drug or ion loading of the HA coating is necessary when using the co-precipitation approach.

Other variations to the disclosed embodiments can be understood and effected by those skilled in the art in practicing the claimed invention, from the study of the drawings, the disclosure, and the appended claims. In the claims the word "comprising" does not exclude other elements or steps and the indefinite article "a" or "an" does not exclude a plurality. Any reference signs in the claims should not be construed as limiting the scope of the claims. The mere fact that certain measures are recited in mutually different dependent claims does not indicate that a combination of these measures cannot be used to advantage. Reference signs in the claims shall not be construed to be limiting in any way.

The invention claimed is:

1. A method of manufacturing an implant for use in a surgical procedure, the method comprising:
    providing a titanium implant substrate,
    anodizing the titanium implant substrate by an electrolytic process in an alkaline liquid,
    blasting the anodized titanium implant substrate,
    soaking the blasted and anodized titanium implant substrate in a NaOH solution for a time period $t_p$ between 1 and 20 minutes without substantially changing the surface microstructure, and
    after the soaking step, coating the blasted and anodized substrate with hydroxyapatite (HA) by depositing a HA coating from a solution between 37° C. and 85° C. to produce the HA coating having a thickness between 0.5 µm and 5 µm.

2. The method according to claim 1,
    wherein the titanium implant substrate is formed of titanium alloy Ti6A1-4V.

3. The method according to claim 1,
    wherein the steps of anodizing and blasting are carried out according to AMS 2488-D resulting in a type II anodized titanium implant substrate.

4. The method according to claim 1,
    wherein the step of coating the substrate with HA is based on crystal growth of HA on a surface of the implant.

5. The method according to claim 1,
    wherein the solution is an aqueous solution containing ions.

6. The method according to claim 1,
    wherein the titanium implant substrate is inserted into the solution for a time period $t_c$, and
    wherein the time period $t_c$ is between 20 h and 80 h.

7. The method according to claim 1,
    wherein the HA coating has a crystalline structure, and
    wherein the HA coating has a thickness which is between 1 µm and 3 µm.

8. The method according to claim 1,
    wherein the time period $t_p$ is between 5 and 15 minutes.

9. The method according to claim 1, the method further comprising:
    incorporating a substance into the HA coating, and
    wherein the substance is a therapeutic agent.

10. The method according to claim 2,
    wherein the steps of anodizing and blasting are carried out according to AMS 2488-D resulting in a type II anodized titanium implant substrate.

11. The method according to claim 1, wherein the solution has a temperature between 50° C. and 80° C.

12. The method according to claim 11, wherein the solution has a temperature between 65° C. and 75° C.

13. The method according to claim 6, wherein the time period $t_c$ is between 40 h and 80 h.

14. The method according to claim 13, wherein the time period $t_c$ is between 60 h and 80 h.

15. The method according to claim 14, wherein the time period $t_c$ is between 65 h and 75 h.

16. The method according to claim 15, wherein the time period $t_c$ is between 70 h and 75 h.

17. The method according to claim 8, wherein the time period $t_p$ is between 8 and 12 minutes.

18. The method according to claim 17, wherein the time period $t_p$ is between 9 and 11 minutes.

19. The method according to claim 9, wherein the therapeutic agent is selected from the group consisting of an osteoporotic drug, bisphosphonates, strontium, PTH, antibiotics, gentamycin, tobramycin, vancomycin, doxycycline, a chemotherapy drug, analgetics, antiphlogistics, metal ions, copper ions, silver ions, organic molecules, and any combination thereof.

* * * * *